Figure 1:
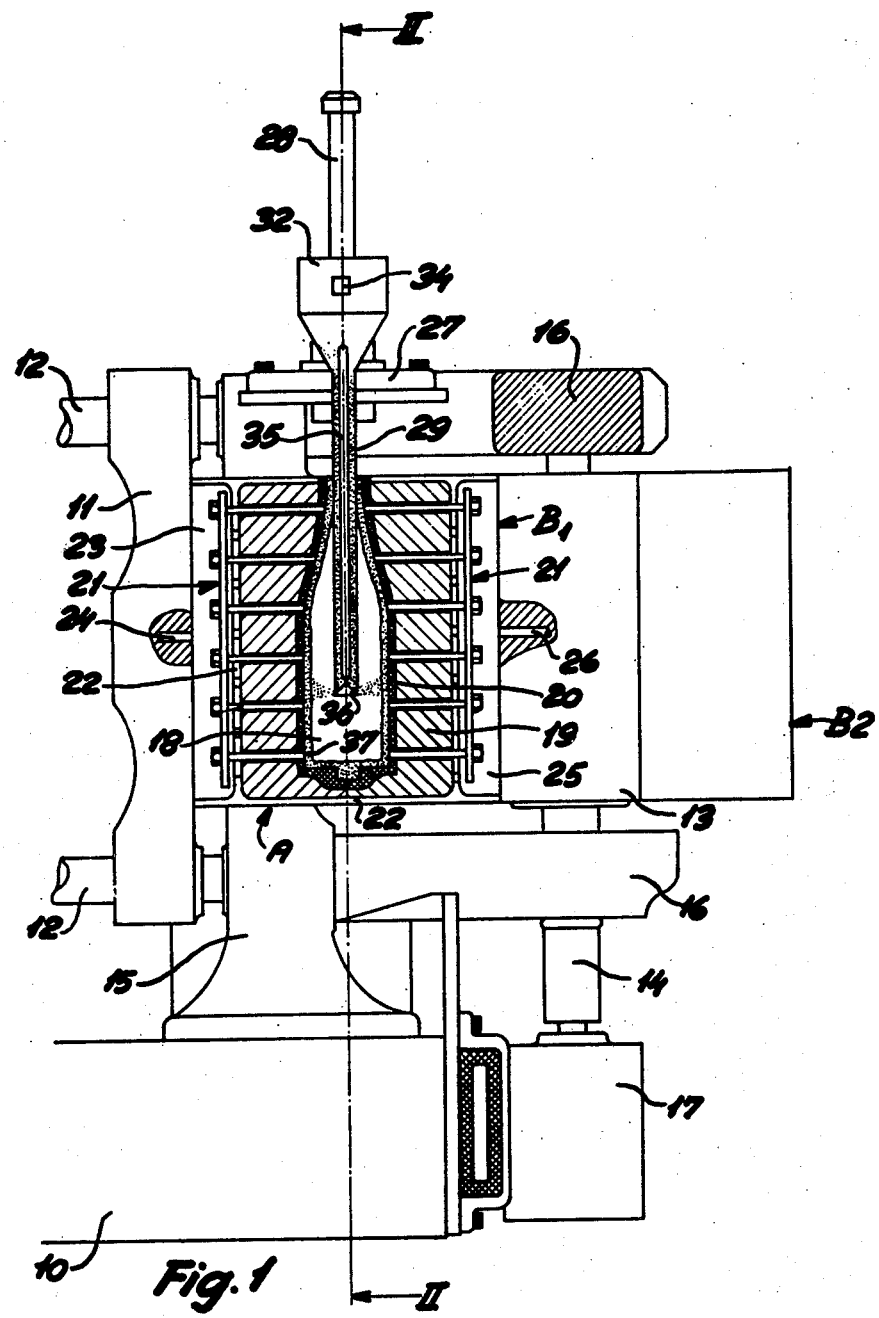

United States Patent [19]

Grove et al.

[11] 4,390,056
[45] Jun. 28, 1983

[54] METHOD AND APPARATUS FOR PRODUCING ONE OR MORE HOLLOW SAND CORES SUITABLE FOR CASTING MOULDS

[75] Inventors: Morgens W. Grove, Bronshoj; Carl-Erik Eriksen, Ballerup, both of Denmark

[73] Assignee: Dansk Industri Syndikat A/S, Herlev, Denmark

[21] Appl. No.: 173,753

[22] Filed: Jul. 30, 1980

Related U.S. Application Data

[63] Continuation of Ser. No. 946,618, Sep. 28, 1978, abandoned, which is a continuation of Ser. No. 700,598, Jun. 28, 1976, abandoned.

[30] Foreign Application Priority Data

Jul. 27, 1975 [DK] Denmark .............. 2920/75

[51] Int. Cl.³ .............. B22C 13/08; B22C 13/12
[52] U.S. Cl. .............. 164/7.1; 164/38; 164/160.1; 164/165; 164/195; 164/202
[58] Field of Search .............. 164/7, 12, 16, 19–23, 164/37, 38, 72, 160, 165, 169, 195, 200, 202, 208, 7.1, 160.1; 222/403, 423; 239/145, 326, 434; 427/180, 181, 622; 425/256, 262, 449

[56] References Cited

U.S. PATENT DOCUMENTS

| | | | |
|---|---|---|---|
| 2,563,643 | 8/1951 | De Ranek | 164/7.1 |
| 3,457,986 | 7/1969 | Andrews | 164/33 X |
| 3,606,159 | 9/1971 | Sutton | 279/434 X |
| 3,798,726 | 3/1974 | Zifferer et al. | 164/16 X |
| 4,002,196 | 1/1977 | Inadama | 164/7.1 |
| 4,020,195 | 4/1977 | Primault | 427/425 X |
| 4,105,725 | 8/1978 | Ross | 164/16 X |

FOREIGN PATENT DOCUMENTS

| | | | |
|---|---|---|---|
| 3301 | 6/1974 | Denmark . | |
| 1103524 | 3/1961 | Fed. Rep. of Germany . | |
| 1251471 | 10/1967 | Fed. Rep. of Germany . | |
| 2444666 | 4/1975 | Fed. Rep. of Germany . | |
| 36-7610 | 6/1961 | Japan | 164/16 |
| 48-30210 | 9/1973 | Japan | 164/16 |
| 50-57919 | 5/1975 | Japan | 164/7.1 |
| 1277407 | 6/1972 | United Kingdom | 164/72 |
| 121229 | of 1959 | U.S.S.R. | 164/228 |

*Primary Examiner*—Gus T. Hampilos
*Attorney, Agent, or Firm*—Fleit, Jacobson & Cohn

[57] ABSTRACT

An apparatus and method for producing one or more hollow sand cores suitable for casting moulds using a bipartite core box defining a mould cavity into which sand and a catalyst or a curing agent are introduced. The method includes the steps of establishing a pressure gradient which decreases from the interior to the exterior of a non-heated core box of porous material; introducing sand and a catalyst or a curing agent into the mould cavity defined by the non-heated core box; and directing the introduced sand and catalyst or curing agent against the interior surface of the non-heated core box, which step of directing, at least in part, is obtained by the pressure gradient established between the interior and exterior of the non-heated core box. The apparatus provides structure for accomplishing the above described method.

6 Claims, 8 Drawing Figures

METHOD AND APPARATUS FOR PRODUCING ONE OR MORE HOLLOW SAND CORES SUITABLE FOR CASTING MOULDS

This is a continuation of application Ser. No. 946,618, filed Sept. 28, 1978, now abandoned, which is a continuation of application Ser. No. 700,598, filed June 28, 1976, now abandoned.

The present invention relates to a method in the production of one or more hollow sand cores suitable for casting moulds by means of a bipartite core box defining a mould cavity.

In using hollow cores in preference to the solid type there is obtained in the case of large cores a considerable saving in both sand and chemicals, and also faster setting owing to the reduced amount of sand used per core. Yet another advantage of using hollow cores is the fact that any gas generated during casting may be removed through the core cavity.

In a prior art method of the subject type a mandrel is inserted into the core box with its axis located in the interface between the two core box halves. In order to be extractable after setting of the sand such a mandrel must be conical, and it is therefore only in connection with certain simple core shapes, such as cylindrical, prismatic, conical or pyramidal, that the advantages obtained are significant.

In another prior art method the so-called shell cores are produced by pouring or injecting sand admixed with a thermosetting binder into a heated core box. When the setting has propagated some distance into the core from the core surface, the entire core box is rotated 180°, and excess sand is poured out. This is a relatively slow process which in addition to heating of the core box requires some rather complicated mechanical equipment for rotating the core box. It has also been suggested to remove excess sand by vacuum rather than pouring out.

It is the object of the invention to provide a method of the type defined above and which makes it possible to produce cores of complex configuration and with cavities of greater transverse dimensions than the opening through which the sand is fed, without using a heated core box.

This object is achieved by inserting a pipe into the mould cavity, from which pipe the sand is thrown or blown at least substantially radially towards the walls of said cavity.

Conveyance of the sand, partly axially into the mould cavity, partly radially towards the walls may be effected in various ways. In some cases the sand passes through the pipe, and in that case the inner end thereof must be moved axially through the mould cavity to achieve even distribution of the sand on the walls of the cavity.

In one practical embodiment of such a method the sand is blown through the pipe against a substantially conical spreader means arranged opposite the inner end of said pipe, whereby the flow of sand is deflected towards the walls of the mould cavity.

In a second embodiment the sand is passed through the pipe down onto a rotating disk arranged opposite the inner end of said pipe from which it is thrown against the walls of the mould cavity.

In a third embodiment the sand is dropped down onto said rotating disk.

In a fourth embodiment the sand is advanced towards the rotating disk by means of a rotary worm.

In a fifth embodiment the sand is caught by a driven impeller arranged opposite the inner end of the pipe, from which it is thrown against the walls of the mould cavity.

However, the sand may also be introduced by retaining same on the outside of a porous pipe by vacuum, whereupon after insertion of the pipe into the mould cavity it is blown or propelled against the walls by abruptly replacing the vacuum by a positive pressure.

Yet another possibility is that air is blown radially from the interior of a porous or perforate pipe against a sand curtain lengthwise of the outside of the pipe.

It applies to all of the aforesaid embodiments according to the invention that the amount of sand used may advantageously be measured out in a manner known per se, whereby the mould cavity will not contain any excess sand to be removed.

Also retention of the layer of sand on the walls of the mould cavity may be accomplished in various ways, e.g. by providing a pressure drop above the layer by means of an air flow through the core box, in which case the latter must be of porous material. The air flow may be produced either by pressure from the inside or by vacuum from the outside.

A further possibility is to provoke fast setting of the sand shell by applying a catalyst simultaneously with the introduction of sand and binder, a porous core box being used.

It is also possible to effect a stratified formation of the core by intermittent supply of sand with binder and spray application of a catalyst between batches of sand supplied. By the catalyst used for hardening the core or cores being introduced through the cavity or cavities thereof the gassing path becomes very short and the hardening process correspondingly fast.

The invention also relates to an apparatus for carrying out the aforesaid method, which apparatus is characterized by comprising a pipe arranged opposite an opening in a bipartite core box so as to be axially movable into and out of the mould cavity of the core box, and by the provision of means for feeding sand lengthwise of the pipe.

In one embodiment of the apparatus according to the invention for carrying out some of the aforesaid embodiments of the method according to the invention there is provided a spreader means opposite the end of the pipe to be inserted into the mould cavity.

In a second embodiment of the apparatus the spreader means is substantially conical, and the means for feeding sand are adapted to inject or propel sand through the pipe.

In a third embodiment the spreader means is a disk rotatable about the axis of the pipe by a motor.

In a fourth embodiment the means for feeding sand are constituted by a rotatable worm arranged in the pipe.

In a fifth embodiment the spreader means is a rotatably mounted driven impeller.

In a sixth embodiment the pipe is porous and sealed at the end to be inserted into the mould cavity, and there are provided a source of vacuum together with a source of pressurized air which are optionally connectable to the pipe.

Figure 2:
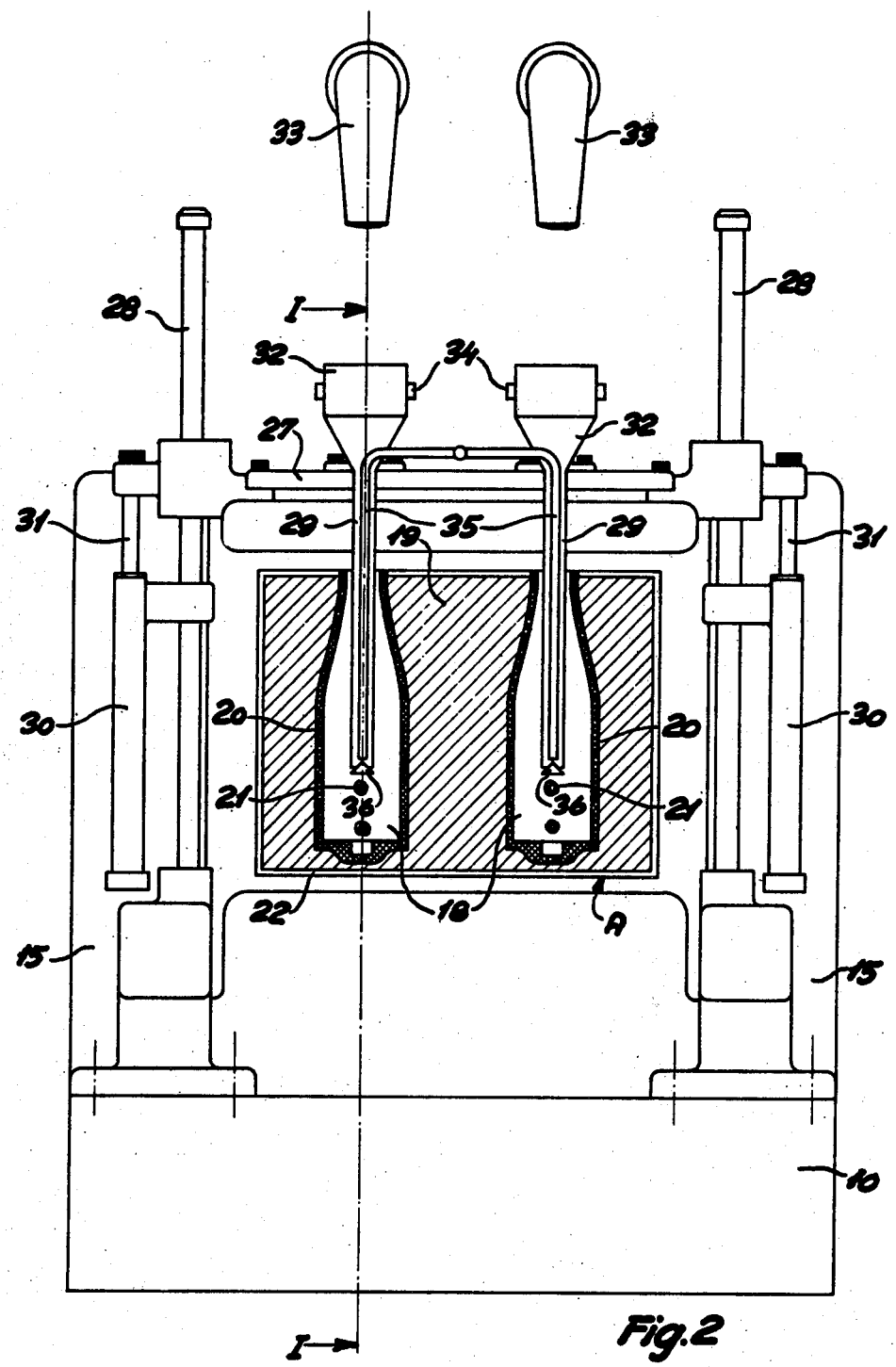
Figure 3:
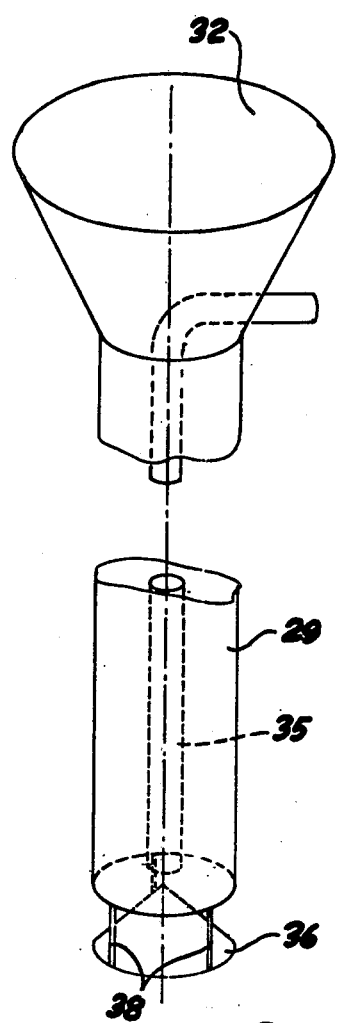
Figure 4:
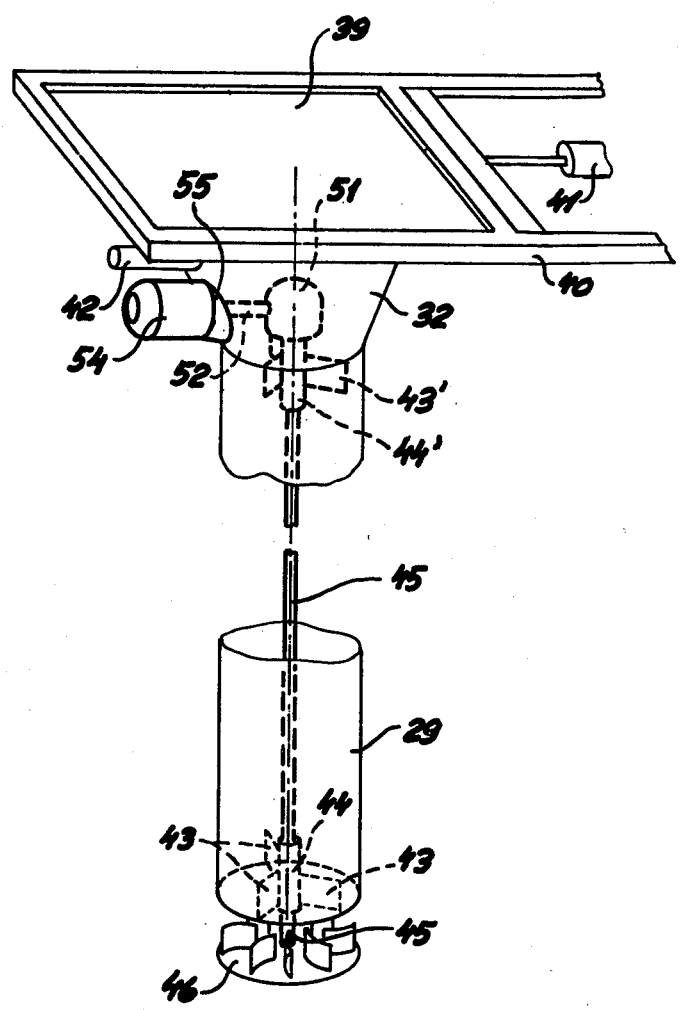
Figure 5:
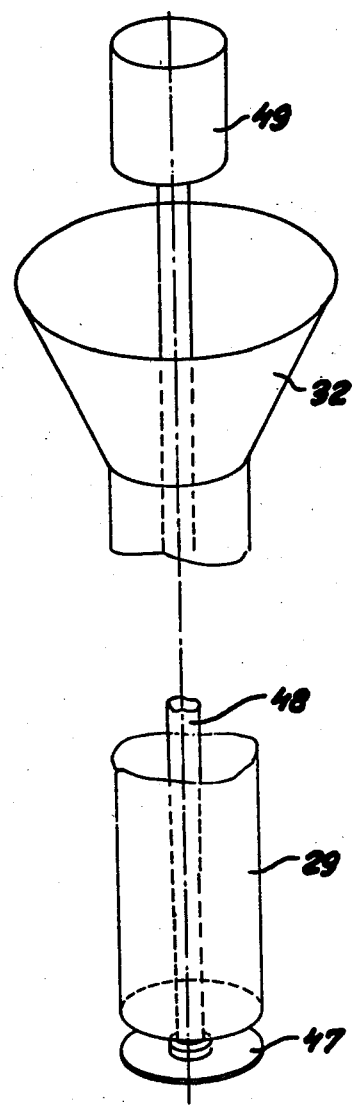
Figure 6:
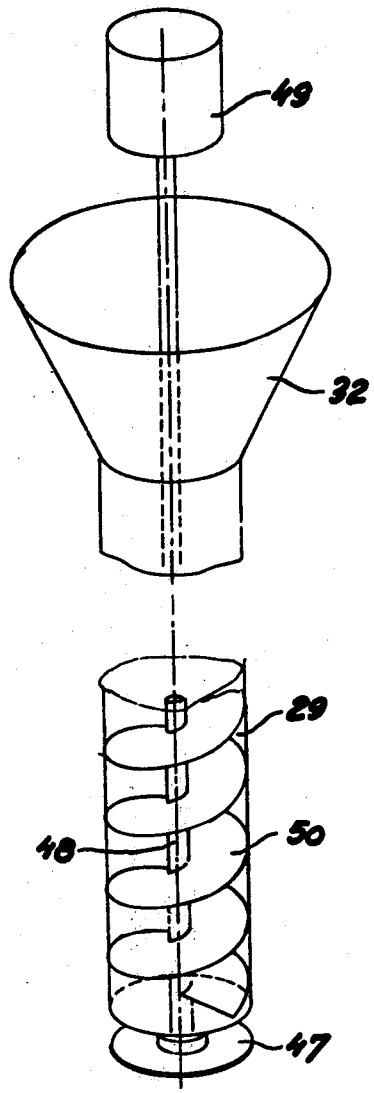

The invention will be further explained below with reference to the drawings, in which FIG. 1 shows part of an embodiment of the apparatus according to the invention partly in lateral view and partly in a sectional view taken along the line I—I of FIG. 2, FIG. 2 shows the machine partly in end view and partly in a section taken along the line II—II of FIG. 1, FIG. 3 is an enlarged perspective of a portion of the embodiment of FIG. 1, FIG. 4 is a perspective of a modified sand feeding assembly usable with the apparatus of FIG. 1, FIG. 5 is a perspective of another modified sand feeding assembly usable with the apparatus of FIG. 1, and FIG. 6 is a perspective of still another modified sand feeding assembly usable with the apparatus of FIG. 1.

Figure 7:
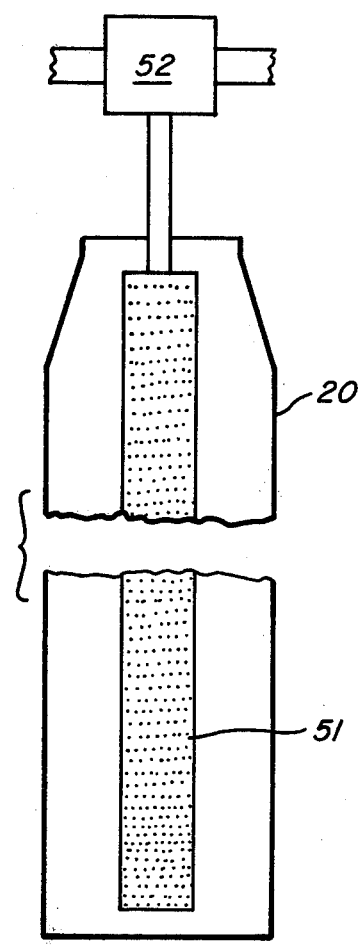
Figure 8:
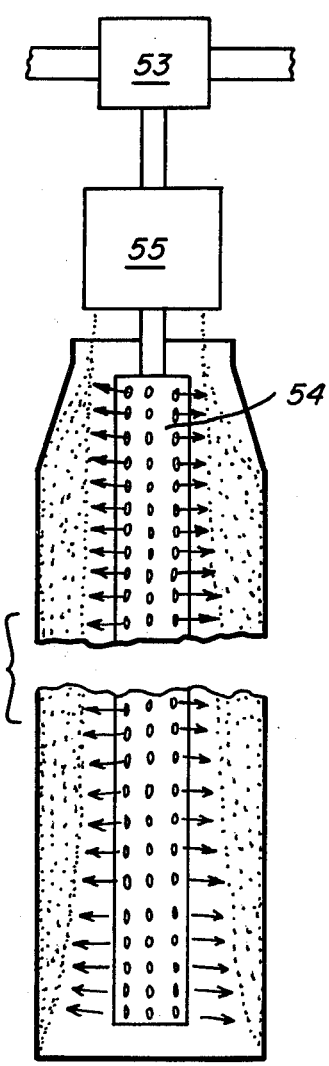

FIG. 7 is a perspective of a modified sand feeding assembly usable with the apparatus of FIG. 1, and FIG. 8 is a perspective of another modified sand assembly usable with the apparatus of FIG. 1.

The core apparatus illustrated in FIGS. 1 and 2 is of the type appearing from FIGS. 4, 8 and 9 in applicant's copending Danish Application No. 3301/74, which corresponds to U.S. Pat. No. 4,079,774. It is mounted on a base frame 10 and includes three core box sections A, B1 and B2, of which A is arranged in a bracket 11 slidably mounted on four guides 12. The two other core box sections B1 and B2 are arranged in opposing relationship on either side of a supporting body 13 which is secured to a vertical shaft 14 rotatably mounted in two horizontal, substantially U-shaped bridge members 16 which in turn are carried by supports 15. The lower end of the shaft 14 is connected to an electric motor 17 mounted on the base frame 10 and which serves to rotate the supporting body 13 with the core box sections B1 and B2. In the position shown in FIG. 1 the core box sections A and B1 abut each other to form a core box having two mould cavities 18, being of bottle shape in the example illustrated.

Each core box section consists of an iron box 22 in which is arranged a body 19 of a coarse porous material and relatively thin layers 20 of a dense porous material, such as ceramics or sintered material, forming the walls of the mould cavities 18. Each core box section includes an ejector assembly 21 for ejecting the finished core.

Between the core box section A and the bracket 11 there is defined a closed chamber 23, which in a manner not further shown may be supplied with vacuum through a passage 24 in the bracket 11. Similarly, the supporting body 13 and each core box section B1 and B2 define a closed chamber, of which only one 25 is seen in FIG. 1. In each of these chambers a vacuum supply passage 26 terminates in the supporting body 13.

For each mould cavity 18 the core box A, B1 includes an upward opening for feeding sand to the cavities, and this is effected by means of an assembly comprising a bridge 27 slidably mounted above the core box A, B1 on two vertical guide posts 28 so as to enable the two vertical pipes 29 supported by the bridge to be moved axially down into and up from the mould cavities 18. The vertical movements of the bridge 27 on the guide posts 28 are produced by means of two pneumatic cylinders 30, the piston rods 31 of which are connected to respective ends of the bridge.

Above the bridge 27 each pipe 29 is provided with a hopper 32 which is fed sand from a charging unit 33 and is equipped with probes 34 for detecting a predetermined sand level and stopping supply of sand in a conventional manner.

Inside and coaxially with each pipe 29 is arranged a pipe 35 for feeding air and catalyst, and these inner pipes are interconnected and may optionally in a manner not shown be connected to a pressurized air source and a catalyst source. The end of the outer pipe 29 includes a conical spreader means 36 whose apex is opposite and proximate to the end of the inner pipe 35.

In the closed position of the core box A, B1, as shown in FIG. 1, and with sand filled into the hoppers 32 up to the predetermined level, which depends on the core weight, the bridge 27 is initially in its upper position in which the pipes 29 clear the core box. The cylinders 30 are actuated to cause the bridge 27 to insert the pipes into the mould cavities 18 until they are slightly spaced from their bottom, after which the pipes are retracted. During this upward and downward movement of the pipes vacuum is supplied to the chambers 23 and 25 together with pressurized air to the inner pipes 35. The vigorous air flow generated thereby from the end of each inner pipe 35 draws by ejector effect the sand down through the outer pipe 29, from which it is forcefully thrown against the spreader means 36 which deflects the flow of sand towards the walls 20 of the mould cavity 18, in which the sand is retained by the vacuum supplied from the outside, gradually forming a hollow core 37. When the pipes are raised to clear the core box the hoppers 32 have been emptied of sand. This is followed by repeating the upward and downward movement of the bridge and the pipes with injection of catalyst through the inner pipes 35 during insertion and injection of scavenging air during retraction. Following this process the hollow core is hardened and ready for use. The core box section A is now retracted, while its ejector assembly 21 is actuated in a not shown conventional manner, after which the supporting body 13 is rotated 180° by the motor 17, whereby the two core box sections B1 and B2 change places. The produced core 37 is now accessible for removal and transfer to a sand mould, e.g. by means of a core mask as shown and described in the aforesaid Danish Application No. 3301/74. Simultaneously therewith there is produced another core in the core box consisting of sections A and B2.

FIG. 3 is an enlarged perspective view of the pipe 29 with hopper 32, inner pipe 35 and conical spreader means 36. This figure also shows three connecting rods 38 by means of which the spreader means 36 is secured to the end of the pipe 29.

FIGS. 4, 5 and 6 are perspective views of other possible embodiments of the sand feeding assembly in combination with the pipe 29.

In the embodiment shown in FIG. 4 a slide 39 is provided above the hopper 32 and which is movable in a frame 40 by means of a pneumatic cylinder 41 between the closed position shown, in which it closes the hopper upwardly, and an open position. A pipe 42 terminates in the side of the upper portion of the hopper 32 for optional feeding of pressurized air and catalyst. In each end of the pipe 29 there is provided by means of three laminar radial arms 43 and 43' respectively a coaxial sleeve 44 and 44' respectively in which is rotatably mounted a shaft 45 extending coaxially through the pipe 29, and the outer end of which shaft is provided with an impeller 46. Above the upper sleeve 44' the shaft 45 is connected through a wheel gearing 51, comprising not shown conical or hyperbolic gearwheels, to a radial shaft 52 driven by a motor 54 mounted in a bracket 55. In this structure the sand is injected through the pipe 29 by pressurized air fed to the pipe 42, and when the driven impeller 46 is caught by the flow of air and sand, it will spread the sand and propel it against the walls of the mould cavity.

In the embodiment shown in FIG. 5 the spreader means is a disk 47 mounted below the end of the pipe 29 at the end of a shaft 48 extending coaxially through the pipe and the hopper 32, being driven a motor 49 mounted above. The sand drops by gravitation down onto the rotating disk 47, from which it is thrown radially outwardly.

The structure shown in FIG. 6 distinguishes from that of FIG. 5 only in that the shaft 48 within the pipe 29 is provided with a worm 50 for forced feeding of sand through the pipe.

In the embodiment shown in FIG. 7, it is likewise possible to introduce the sand into the core box by means of a porous pipe 51 which is connectable to a device 52 which selectively supplies a vacuum or compressed air to pipe 51. The outside of pipe 51 retains a layer of sand by means of a vacuum fed to the interior of the pipe. After inserting the pipe into the mould cavity, the vacuum present is abruptly replaced by compressed air, whereby the sand from the outside of the pipe is thrown outwardly against the walls of the cavity. This effect is enhanced by the vacuum fed from the outside through the core box and which primarily serves to retain the sand on the cavity walls.

In the embodiment of FIG. 8, air is blown radially from the interior of a porous or perforate pipe 54 against a sand current emanating from a supply source 55 and passing lengthwise of the outside of the pipe 54.

There could be imagined other embodiments of the means for supplying and spreading sand from the pipe 29 than those illustrated and explained above, and also retention of the sand on the walls of the mould cavity may be effected by means other than a vacuum supplied from the outside. In addition to the aforesaid applications of compressed air supplied from the inside and of catalyst supplied from the inside alternately with sand and binder, the said retention may be effected by means of centrifugal effect produced by rotation of the core box and which makes possible supply of catalyst from the outside. The catalyst may also be supplied together with sand and binder.

What we claim is:

1. A method for producing one or more hollow sand cores suitable for casting moulds by means of a bipartite core box (A, B) defining a mould cavity having an interior with bottom and side surfaces into which sand, binder, and catalyst or a curing agent are introduced comprising the steps of:
   (1) establishing a pressure gradient which decreases from the interior to the exterior of a non-heated core box (A, B) of porous material, at least a portion of the porous material being coarse so that the pressure gradient is readily transmitted through walls of the core box,
   (2) introducing sand, binder, and a catalyst or a curing agent into the mould cavity defined by said non-heated core box (A, B), the sand being introduced into the mould cavity as a layer of sand on the outside of a porous pipe and being retained thereon by means of vacuum maintained in the interior of the pipe,
   (3) directing the introduced sand, binder, and catalyst or curing agent against the side surfaces of the interior of the non-heated core box (A, B) which step of directing, at least in part, is obtained by the pressure gradient established between the interior and exterior of the non-heated core box (A, B), and by abruptly replacing the vacuum in the pipe by an overpressure whereupon the sand is blown against the interior surface of the non-heated core box, and
   (4) using the pressure gradient to hold the introduced sand, binder, and catalyst or curing agent against the side surfaces of the interior while they solidify to form the hollow sand core.

2. A method for producing one or more hollow sand cores suitable for casting moulds by means of a bipartite core box (A, B) defining a mould cavity having an interior with bottom and side surfaces into which sand, binder, and catalyst or a curing agent are introduced comprising the steps of:
   (1) establishing a pressure gradient which decreases from the interior to the exterior of a non-heated core box (A, B) of porous material, at least a portion of the porous material being coarse so that the pressure gradient is readily transmitted through walls of the core box,
   (2) introducing sand, binder, and a catalyst or a curing agent into the mould cavity defined by said non-heated core box (A, B),
   (3) directing the introduced sand, binder, and catalyst or curing agent against the side surfaces of the interior of the non-heated core box (A, B) which step of directing, at least in part, is obtained by the pressure gradient established between the interior and exterior of the non-heated core box (A, B), the introducing and the directing of the introduced sand including positioning a pipe in the mould cavity with its bottom close to the bottom of the mould cavity, progressively removing the pipe from the mould cavity while the sand is being directed from the bottom of the pipe against the interior surface of the mould cavity, the introducing and the directing of the introduced catalyst or curing agent including progressively reintroducing the pipe into the mould cavity while the catalyst or curing agent is being directed from the bottom of the pipe against the sand positioned on the interior surface of the mould cavity, and
   (4) using the pressure gradient to hold the introduced sand, binder, and catalyst or curing agent against the side surfaces of the interior while they solidify to form the hollow sand core.

3. An apparatus for producing one or more hollow sand cores suitable for casting moulds by means of a bipartite core box (A, B) defining a mould cavity having an interior with bottom and side surfaces into which sand, binder, and a catalyst or a curing agent are introduced comprising:
   (1) means for establishing a pressure gradient which decreases from the interior to the exterior of a non-heated core box (A, B) of porous material,
   (2) means for introducing sand, binder, and a catalyst or a curing agent into the mould cavity defined by said non-heated core box (A, B), said means for introducing comprising a sand supply pipe arranged to be inserted into the mould cavity, said sand supply pipe being porous and closed at the end to be inserted into the mould cavity, and said apparatus includes a source of vacuum and a source of compressed air which are selectively connectable to the pipe in such manner that vacuum holds sand on the pipe when it is inserted into the mould cavity and compressed air replaces the vacuum after the pipe has been introduced into the mould cavity, and (3) means for directing the introduced sand, binder, and catalyst or curing agent against the side surfaces of the interior of the non-heated core box (A, B) which step of directing, at least in part, is obtained by the pressure gradient established between the interior and exterior of the non-heated core box (A, B), the pressure gradient holding the introduced sand, binder, and a catalyst or a curing agent while they solidify to form the hollow sand core.

4. An apparatus according to claim 3, wherein said means for establishing a pressure gradient includes means for establishing a vacuum at the exterior of the core box.

5. An apparatus for producing one or more hollow sand cores suitable for casting moulds by means of a bipartite core box (A, B) defining a mould cavity into which sand, binder, and a catalyst or a curing agent are introduced comprising:
 (1) means for establishing a pressure gradient that decreases from the interior to the exterior of a non-heated core box (A, B) of porous material,
 (2) means for introducing a mixture of sand and a cold curing binder into the mould cavity defined by said non-heated core box (A, B), and for directing said mixture against the interior surface of the non-heated core box (A, B),
 (3) means for directing the introduced mixture against the interior surface of the non-heated core box (A, B) on which surface the mixture is held at least partly by means of the pressure gradient established between the interior and exterior of the non-heated core box (A, B), said means for introducing comprising a sand supply pipe arranged to be inserted into the mould cavity, said sand supply pipe being porous and closed at the end to be inserted into the mould cavity and said apparatus includes a source of vacuum and a source of compressed air which are selectively connectable to the pipe in such manner that vacuum holds sand on the pipe when it is inserted into the mould cavity and compressed air replaces the vacuum after the pipe has been introduced into the mould cavity, and
 (4) means for introducing a catalyst or a curing agent into said mould cavity.

6. An apparatus according to claim 5, wherein said means for establishing a pressure gradient includes means for establishing a vacuum at the exterior of the core box.

* * * * *

UNITED STATES PATENT AND TRADEMARK OFFICE
CERTIFICATE OF CORRECTION

PATENT NO. : 4,390,056
DATED : June 28, 1983
INVENTOR(S) : Mogens W. GROVE et al It is certified that error appears in the above-identified patent and that said Letters Patent are hereby corrected as shown below:

On the title page, after "[75] Inventors" correct the first inventor's given name to be -- Mogens-- and Foreign Application Priority Data should read:

--June 27, 1975[DK] Denmark ............ 2920/75

Signed and Sealed this

Fourteenth Day of February 1984

[SEAL]

Attest:

GERALD J. MOSSINGHOFF

Attesting Officer

Commissioner of Patents and Trademarks